US009540609B2

(12) United States Patent
Burton et al.

(10) Patent No.: US 9,540,609 B2
(45) Date of Patent: Jan. 10, 2017

(54) ***LACTOBACILLUS RHAMNOSUS* FOOD GRADE BACTERIA**

(71) Applicant: Compagnie Gervais Danone, Paris (FR)

(72) Inventors: Jeremy Burton, London (CA); Marc Monaches, Oakville (CA); Gregor Reid, Komoka (CA); Tamara Smokvina, Orsay (FR); Johan Van Hylckama Vlieg, Marly le Roi (FR); Jordan Bisanz, St. Thomas (CA)

( * ) Notice: Subject to any disclaimer, the term of this patent is extended or adjusted under 35 U.S.C. 154(b) by 0 days.

(21) Appl. No.: 14/390,018

(22) PCT Filed: Apr. 5, 2013

(86) PCT No.: PCT/IB2013/052739
§ 371 (c)(1),
(2) Date: Oct. 1, 2014

(87) PCT Pub. No.: WO2013/150497

PCT Pub. Date: Oct. 10, 2013

(65) Prior Publication Data

US 2015/0079236 A1    Mar. 19, 2015

Related U.S. Application Data

(60) Provisional application No. 61/620,796, filed on Apr. 5, 2012.

(51) Int. Cl.
| | |
|---|---|
| *A23C 9/12* | (2006.01) |
| *C12N 1/20* | (2006.01) |
| *C12N 15/74* | (2006.01) |
| *C12N 1/00* | (2006.01) |
| *C12N 15/00* | (2006.01) |
| *A01N 63/00* | (2006.01) |
| *A61K 48/00* | (2006.01) |
| *C12R 1/225* | (2006.01) |
| *A23C 9/123* | (2006.01) |
| *A61K 35/747* | (2015.01) |
| *A62D 3/02* | (2007.01) |
| *A61K 35/74* | (2015.01) |
| *C12N 15/10* | (2006.01) |
| *A61K 38/00* | (2006.01) |
| *C12N 15/70* | (2006.01) |
| *A23K 1/00* | (2006.01) |
| *C12N 15/86* | (2006.01) |

(52) U.S. Cl.
CPC .............. *C12N 1/20* (2013.01); *A23C 9/1234* (2013.01); *A61K 35/747* (2013.01); *A62D 3/02* (2013.01); *C12N 15/746* (2013.01); *C12R 1/225* (2013.01); *A23K 1/009* (2013.01); *A23Y 2220/73* (2013.01); *A61K 35/74* (2013.01); *A61K 38/00* (2013.01); *C12N 15/102* (2013.01); *C12N 15/70* (2013.01); *C12N 15/86* (2013.01)

(58) Field of Classification Search
CPC ............ A23V 2002/00; A61K 2300/00; A61K 35/747; A61K 35/745; A23L 1/3014; A23C 9/1234; A23Y 2220/73; A62D 3/02; C12N 15/76
See application file for complete search history.

(56) References Cited

U.S. PATENT DOCUMENTS

| | | |
|---|---|---|
| 5,531,988 A | 7/1996 | Paul et al. |
| 6,080,401 A | 6/2000 | Reddy et al. |
| 6,479,051 B1 | 11/2002 | Bruce et al. |
| 6,641,808 B1 | 11/2003 | Bojrab et al. |
| 2015/0191691 A1* | 7/2015 | Bisanz ................... C12R 1/225 424/93.45 |

OTHER PUBLICATIONS

Mehran Pazirandeh, Bridget M. Wells and Rebecca L. Ryan, Appl. Environ. Microbiol. 1998, 64(10):4068.
Jatindra N. Bhakta, et al., "Isolation and Probiotic Characterization of Arsenic-Resistant Lactic Acid Bacteria for Uptaking Arsenic," International Journal of Biological, Biomolecular, Agricultural, Food and Biotechnological Engineering, vol. 4, No. 11, 2010, pp. 831-838.
Hani El-Nezami et al., "Ability of *Lactobacillus* and *Propionibacterium* Strains to Remove Aflatoxin B1 from the Chicken Duodenum," Journal of Food Protection, vol. 63, No. 4,2000, pp. 549-552.
S. Fuchs, et al., "Detoxification of patulin and ochratoxin A, two abundant mycotoxins, by lactic acid bacteria," Food and Chemical Toxicology 46 (2008) 1398-1407.
T. Halttunen, et al., "Rapid removal of lead and cadmium from water by specific lactic acid bacteria," International Journal of Food Microbiology 114 (2007) 30-35.
Teemu Halttunen, et al., "Arsenic removal by native and chemically modified lactic acid bacteria," International Journal of Food Microbiology 120 (2007) 173-178.
Carolyn Haskard, et al., "Factors affecting the sequestration of aflatoxin by *Lactobacillus rhamnosus* strain GG," Chemico-Biological Interactions 128 (2000) 39-49.
A Hernandez-Mendoza, et al., "Screening of *Lactobacillus casei* strains for their ability to bind aflatoxin B1," Food and Chemical Toxicology 47 (2009) 1064-1068.
Fandi Ibrahim, et al., "Probiotic bacteria as potential detoxification tools: assessing their heavy metal binding sotherms," Can. J. Microbiol., vol. 52, pp. 877-885 (2006).
Maurice Ndagijimana, et al., "Effect of a synbiotic food consumption on human gut metabolic profiles evaluated by 1H Nuclear Magnetic Resonance spectroscopy," International Journal of Food Microbiology 134 (2009) 147-153.
Maritsa Pierides, et al., "Ability of Dairy Strains of Lactic Acid Bacteria to Bind Aflatoxin M1 in a Food Model," Journal of Food Protection, vol. 63, No. 5,2000, pp. 645-650.
Mani Rajkumar, et al., "Potential of siderophore-producing bacteria for improving heavy metal phytoextraction," rends in Biotechnology vol. 28 No. 3, (2009) pp. 142-149.

(Continued)

*Primary Examiner* — Gary Nickol
*Assistant Examiner* — Lakia Tongue
(74) *Attorney, Agent, or Firm* — Law Office of Salvatore Arrigo and Scott Lee, LLP

(57) ABSTRACT

The present invention relates to food-grade bacteria strain being capable of removing mercury from an aqueous environment.

15 Claims, 2 Drawing Sheets

(56) References Cited

OTHER PUBLICATIONS

Abou-Baker Salim, et al., "Effect of Lactic Acid Bacteria against Heavy Metals Toxicity in Rats," Journal of American Science, 2011;7(4), pp. 264-274.
Donald Sharp, "Environmental TOxINS, A Potential Risk Factor for Diabetes Among Canadian Aboriginals," International Journal of Circumpolar Health 68:4 2009, pp. 316-326.
Jay Shankar Singh, et al., "Genetically engineered bacteria: An emerging tool for environmental remediation and future research perspectives," Gene 480 (2011) 1-9.
M. A. Brudnak, "Probiotics as an adjuvant to detoxification protocols," Medical Hypotheses (2002) 58(5), 382-385.
K. Kajander, et al., "Effects of multispecies probiotic supplementation on intestinal microbiota in irritable bowel syndrome," Aliment Pharmacol Ther 26, 463-473 (2007).
Kathryn R. Mahaffey, "Mercury Exposure: Medical and Public Health Issues," Transactions of the American Clinical and Climatological Association, vol. 116, 2005 127-154.
Lawrence Wilson, "Toxic metals and Detoxification," http://drlwilson.com/articles,TOXIC%20METALS.htm, 2015, pp. 1-60.
Office Action mailed Mar. 8, 2016, in U.S. Appl. No. 14/390,685.

\* cited by examiner

LACTOBACILLUS RHAMNOSUS FOOD GRADE BACTERIA

FIELD OF THE INVENTION

The present invention relates to food grade bacteria for improving detoxification. More particularly, the present invention relates to a food grade bacteria, or extracts thereof, capable of removing mercury from an aqueous environment to which the food-grade bacteria is exposed to.

BACKGROUND OF THE INVENTION

Humans and animals in general, are exposed to many toxic compounds that contaminate the environment, food chain, water supply and various items that are part of everyday life. These range in number, type and exposure from ingredients in toothpaste and shampoos to drugs and pathogens in well-water. Amongst Canadian First Nation and Inuit populations, environmental toxins are risk factors for other highly prevalent diseases, especially type 2 diabetes [Sharp D. Environmental toxins, a potential risk factor for diabetes among Canadian Aboriginals. Int J Circumpolar Health. 2009; 68(4):316-26]. A large over-the-counter consumer market has arisen under the guise of 'detox', but most of the products have no rationale or clinical evidence to support their use. The concept of detox has great appeal to consumers, both the health-conscious and others concerned with the growing number of stories in the media about pollution and diseases related to toxic substances. Thus, there is substantial interest in this area, few effective products and a growing need.

The replenishment or boosting of the beneficial organisms through administration of probiotics has become feasible in Canada relatively recently, and has led to much interest amongst consumer and healthcare professionals. Indeed, probiotics are one of the fastest growing food segments in North America. However, gaining insight into the mechanisms by which indigenous microbes and exogenous probiotics affect the subject has been limited.

Probiotic *lactobacilli* and bifidobacteria have been shown to help manage several gut pathologies. For example, U.S. Pat. No. 6,641,808 disclosing the use of *lactobacilli* for the treatment of obesity; U.S. Pat. No. 5,531,988, discloses a mixture of an immunoglobulin and a bacterium, such as *lactobacilli* or *bifidobacterium* or mixtures thereof, that may be used to treat diarrhea, constipation, and gas/cramps; U.S. Pat. No. 6,080,401 discloses a combination of probiotics having *Lactobacillus acidophilus* and *Bifidobacterium bifidus* and herbal preparations for aiding in weight loss, and so forth.

The ability of probiotic products to ameliorate toxins has been much less studied, but nevertheless has some foundation. For example, *lactobacilli* and/or bifidobacteria have been found to alter the subject's intestinal metabolic signature [Ndagijimana, M. Laghi L, Vitali B, Placucci G, Brigidi P, Guerzoni M E. Effect of synbiotic food consumption on human gut metabolic profiles evaluated by 1H nuclear magnetic resonance spectroscopy. Int J Food Microbiol. 2009; 134: 147-153]; bind to aflatoxin (*Lactobacillus* strains) [Hernandez-Mendoza A, Garcia H S, Steele J L. Screening of *Lactobacillus casei* strains for their ability to bind aflatoxin B1. Food Chem Toxicol. 2009; 47(6):1064-8]; and detoxify or bind and negate other mycotoxins (*B. animalis*) [Fuchs S, Sontag G, Stidl R, Ehrlich V, Kundi M, Knasmüller S. Detoxication of patulin and ochratoxin A, two abundant mycotoxins, by lactic acid bacteria. Food Chem Toxicol. 2008; 46(4):1398-407].

In summary, the problem associated with toxic compounds is real, and of growing concern to consumers.

Heavy Metals

Heavy metal toxicity is one of the largest health risks in the 21st century. Consumption of lead and cadmium through environmental exposure and diet has been directly responsible for poor health outcomes including: impaired neurological function and loss of IQ, osteoporosis, lung and kidney cancer.

Heavy metals such as lead and cadmium are present in the natural environment, and therefore many bacteria over time have developed mechanisms of resistance to these metals which generally include actively precipitating and sequestering the metals intra/extra cellular or the active efflux of metals out of the cell cytoplasm. Non-food grade bacteria have been investigated for their use in sequestration and detoxification of heavy metals and have shown success.

Mercury

Mercury is one of the most toxic substances known to man and its consumption by a subject is linked to poor health outcomes including altered neurological development in children. Yet, North Americans and Europeans are estimated to consume 6.7 µg daily of inorganic mercury and methylmercury (World Health Organization, 1991).

Mercury is present in the natural environment, and as such, many bacteria have adopted mechanisms of resistance to it, which generally reduce mercury levels in the surrounding environment. Many non-food grade bacteria have been investigated for their use in sequestration and detoxification of mercury and mercury compounds in the environment however the application of food grade bacteria has not been demonstrated to date.

Arsenic

Arsenic is a metalloid element which commonly comes in two oxidation states: arsenate (As V) and arsenite (As III). Arsenic is found distributed globally often in the earth's crust, it is highly soluble in water and is found in high concentrations in ground water. Arsenic toxicity has been linked to a number of cases and is known to cause organ failure, cancer and death. Main routes of exposure is through ingestion via diet, often arsenic contaminated waters are used for irrigation of farmland resulting in accumulation of the metal in plants and food.

Pesticides

Pesticides such as malathion and parathion fall into the class of organophosphate compounds and act as cholinesterase inhibitors. Malathion is one of the most widely used pesticides in the U.S., and parathion use has recently been limited and is not used in many developed nations due to high toxicity. However, produce imports still consistently detect levels of parathion on produce and it is used in some rare instances in North America.

Major routes of public exposure is through consumption via diet. Agricultural workers and industrial workers are at increased risk of exposure through work place by absorption or inhalation if safety protocols not properly followed.

In view of the problems associated to the exposure of any of the above toxic compounds, it would be advantageous to provide for food grade bacteria that can sequester toxic compounds, including heavy metals, mercury, arsenic, pesticides, such as malathion and parathion, or a combination thereof, from the gastrointestinal tract of a subject to reduce the amount of the toxic compound available to be absorbed by the subject, while detoxifying the toxic compounds directly reduces the toxicity of toxic compounds available to be absorbed by the subject. There is a need in bacteria strains that present improved heavy metals, preferably mercury, removal capabilities.

SUMMARY OF THE INVENTION

It is an object of the present invention to provide for food-grade bacteria or extracts thereof for the removal and/or neutralization of toxic products from an environment or substance to which the food-grade bacteria is exposed to, that solve the deficiencies inherent in traditional detoxification treatments.

The present invention provides an effective treatment for removal and/or neutralization of toxic products found in the internal environment of animals, in the environment to which the animal is exposed or in substance ingested by the animals that may avoid adverse side effects, is reasonable in cost, and may be beneficial in reducing the risk of diseases related to said toxic products. Further, the present invention is relatively easy to manufacture and deliver to a subject.

It is an object of the present invention to provide for food grade bacteria, or extracts thereof, to detoxify and/or sequester toxic compounds, including heavy metals, mercury, arsenic and pesticides, with the application of reducing a subject's toxic compounds uptake.

The present invention addresses the need for improved bacteria strains to do so, particularly for mercury removal, with a *Lactobacillus rhamnosus* food grade bacteria strain, being the strain deposited with the CNCM under number I-4719.

The present invention also concerns method for obtaining a strain of *Lactobacillus rhamnosus* comprising a step of mutagenesis or genetic transformation of the *Lactobacillus rhamnosus* strain deposited with the CNCM under number I-4719. The obtained strain can be referred to as a "modified" strain, encompassing mutant strains and genetically transformed strains.

The present invention also concerns a modified *Lactobacillus rhamnosus* strain that is obtained by the method above. The modified strain is typically capable of removing mercury from an aqueous environment.

The present invention also concerns a method for obtaining a cell fraction, comprising the steps of:
  a) culturing a *Lactobacillus rhamnosus* strain as mentioned above, and
  b) recovering the cell fraction from the culture in step a).

The present invention also concerns a cell fraction, which is obtained by the method above. The cell fraction is typically capable of removing mercury from an aqueous environment.

The present invention also concerns a composition comprising a *Lactobacillus rhamnosus* strain as mentioned above.

Hereafter, unless otherwise provided, the food grade bacteria is the *Lactobacillus rhamnosus* strain being the strain deposited with the CNCM under number I-4719, or mutagenesis or genetic transformation products thereof, or cell fractions thereof.

The strain CNCM I-4719 allows a surprisingly improved mercury removal, as compared to other *Lactobacillus rhamnosus* strains. Examples of comparative strains allowing less mercury removal are the strains listed in Table 1 below.

As such, in one embodiment, the present invention provides food-grade bacteria or extracts thereof for removing of toxic compounds from a substance or environment to which the food-grade bacteria is exposed to.

In another embodiment, the present invention provides for a composition comprising a food-grade bacteria and a suitable carrier, whereby the composition comprises an effective dose of the food-grade bacteria to remove a toxic compound from a substance or environment to which the food-grade bacteria is exposed to.

In one embodiment of the present invention the substance is an edible or drinkable substance.

In another embodiment, the substance is a raw material used to manufacture the edible or drinkable substance.

In another embodiment of the present invention the environment is the gastrointestinal tact of a subject.

In another embodiment of the present invention the environment is an aquatic environment in which a subject lives.

In one embodiment of the present invention, the food grade bacteria or extract thereof are provided in a nutritional composition comprising the food-grade bacteria or extract thereof and a carbohydrate enriched media.

In one embodiment, the composition comprises a combination of two or more different species of food-grade bacteria.

In another embodiment, the present invention further provides for a method for reducing a subject uptake of toxic compounds consumed by the subject. The method, in one embodiment, comprises administering to the subject an effective dose of a food-grade bacteria or extract thereof capable of sequestering the toxic compound consumed by the subject.

In another embodiment, the present invention provides for a method for removing a toxic compound from a substance which is contaminated with said toxic compound comprising contacting the substance with food-grade bacteria or extract thereof capable of removing the toxic compound from the substance.

In another embodiment, the present invention provides for a method of reducing the toxic effects of a toxic compound in a subject, the method comprising: administering to the subject a therapeutically effective amount of food-grade bacteria of Table 1 or any combination thereof.

In one embodiment of the methods of the present invention, the food-grade bacteria comprise a combination of two or more different species of food-grade bacteria.

In one aspect of the present invention the toxic compound includes a heavy metal.

In another aspect of the present invention, the toxic compound includes a heavy metal and the food-grade bacteria comprise dead bacteria.

In another aspect of the present invention, the toxic compound includes a heavy metal and the food-grade bacteria comprise live bacteria.

In one another of the present invention, the toxic compound includes a heavy metal and the food-grade bacteria comprise a mixture of dead bacteria and live bacteria.

In another aspect of the present invention the heavy metal is cadmium.

In another aspect of the present invention the heavy metal is lead.

In another aspect of the present invention the toxic compound includes mercury.

In another aspect of the invention the mercury is inorganic mercury.

In another aspect of the invention the mercury is organic mercury.

In one aspect of the present invention, the toxic compound includes mercury and the food-grade bacteria comprise dead bacteria.

In one aspect of the present invention, the toxic compound includes mercury and the food-grade bacteria comprise live bacteria.

In one aspect of the present invention, the toxic compound includes mercury and the food-grade bacteria comprise a mixture of dead bacteria and live bacteria.

In another aspect of the present invention the toxic compound includes arsenic.

In one aspect of the present invention, the toxic compound includes arsenic and the food-grade bacteria comprise dead bacteria.

In one aspect of the present invention, the toxic compound includes arsenic and the food-grade bacteria comprise live bacteria.

In another aspect of the present invention the toxic compound includes a pesticide.

In one aspect of the present invention, the toxic compound includes a pesticide and the food-grade bacteria comprise dead bacteria.

In one aspect of the present invention, the toxic compound includes a pesticide and the food-grade bacteria comprise live bacteria.

In another aspect of the present invention the pesticide is selected from malathion or parathion.

In another aspect of the present invention, the toxic compound includes endotoxins.

In another aspect of the present invention, the toxic compound includes aflatoxin.

In another aspect of the present invention, the toxic compound includes heterocyclic aromatic amines.

In another aspect of the present invention, the toxic compound includes acrylamide

BRIEF DESCRIPTION OF THE FIGURES

The present invention will become more fully understood from the detailed description given herein and from the accompanying drawings, which are given by way of illustration only and do not limit the intended scope of the invention.

DETAILED DESCRIPTION OF THE INVENTION

Definitions

Figure 1:
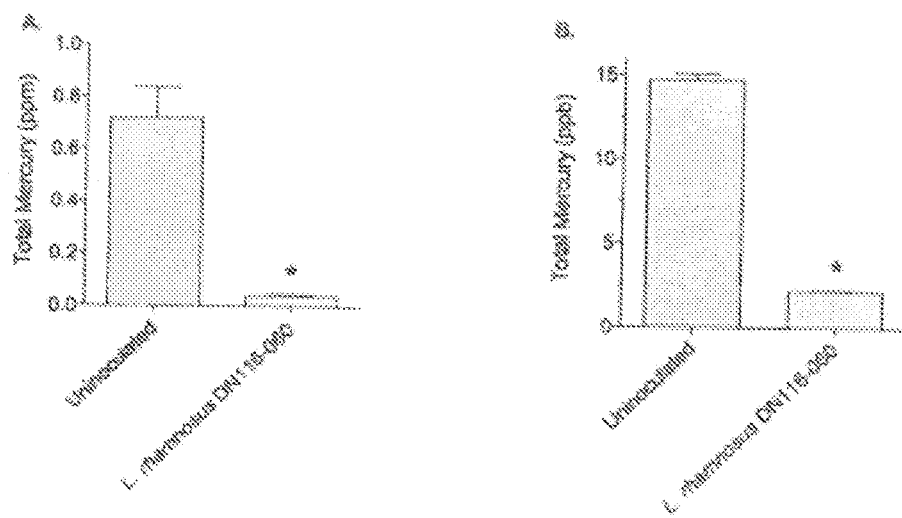
FIG. 1A is a graph illustrating the ability of a food grade bacterium of the present invention to remove $Hg^{2+}$ from a solution having a 1 part per million (ppm) $Hg^{2+}$ inoculum (error bars±SEM; * signifies significant (p<0.05) difference by an unpaired T-test).
FIG. 1B is a graph illustrating the ability of a food grade bacterium of the present invention to remove $Hg^{2+}$ from a solution having a 15 part per billion (ppb) $Hg^{2+}$ inoculum (error bars±SEM; * signifies significant (p<0.05) difference by an unpaired T-test).

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise.

The expression "food grade bacteria" refers to any bacteria, alive or dead, that have no harmful effect on human health or that have a GRAS (generally recognized as safe) status.

The term "probiotic" as used in this document refers to food-grade bacteria which perform beneficial functions for the subject organisms when they are present and alive in viable form.

"Food production animal" is used herein to describe any animal that is prepared and used for human consumption. A food production animal can be, but not limited to, a ruminant animal such as beef and dairy cattle, pigs, lamb, chicken, turkey or any other fowl, or aquatic animals including shrimp, lobster or fish used for human consumption.

"Subject" or "subjects" are used herein to describe a member of the animal kingdom, including food production animals and humans.

The *Lactobacillus rhamnosus* food grade bacteria strain I-4719 and modifications The *Lactobacillus rhamnosus* strain is deposited, according to the Budapest Treaty, at CNCM (Collection Nationale de Cultures de Microorganismes, 25 rue du Docteur Roux, Paris) on Mar. 5, 2013, under the accession number CNCM I-4719. This strain is also referred to as "DN 116-060" or R37.

This strain CNCM I-4719 has the following characteristics:

Colony morphology (on solid neutral MRS+cysteine, 72 h at 37° C., anaerobic under CO2 conditions): Irregular, shiny, white colonies 2 mm Microscopic morphology (on liquid neutral MRS+cysteine, 16 h at 37° C., aerobic conditions): Small, thin, bipolar sticks, in short chains or in cluster Fermentation (and identification) of the following substrates (on an API 50 CH strip, in API MRS medium at 37° C. for 48 h): D-ribose, D-galactose, D-glucose, D-fructose, D-mannose, L-sorbose, L-rhamnose, Inositol, D-mannitol, D-sorbitol, Methyl-alphaD-Mannopyranoside, Methyl-alphaD-Glucopyranoside, N-AcetylGlucosamine, Amygdalin, Arbutin, Esculin, Salicin, D-cellobiose, D-maltose, D-lactose, D-saccharose, D-threhalose, D-melezitose, Gentiobiose, D-turanose, D-tagatose, potassium Gluconate.

This strain is capable of removing mercury from an aqueous environment.

As used herein, the term "removing mercury from an aqueous environment" refers to a removal of mercury that can be for tested as described in at least one of the examples below.

The present invention also encompasses mutant strains or genetically transformed strains derived from the parent strain CNCM I-4719. These mutant or genetically transformed strains can be strains wherein one or more endogenous gene(s) of the parent strain has (have) been mutated, for instance to modify some of its metabolic properties (e.g., its ability to ferment sugars, its resistance to acidity, its survival to transport in the gastrointestinal tract, its postacidification properties or its metabolite production). They can also be strains resulting from the genetic transformation of the parent strain CNCM I-4719 by one or more gene(s) of interest, for instance in order to confer to said genetically transformed strains additional physiological features, or to allow it to express proteins of therapeutic or vaccinal interest that one wishes to administer through said strains. These strains can be obtained from the CNCM I-4719 strain by means of the conventional techniques for random or site-directed mutagenesis and genetic transformation of *Lactobacilli*, such as those described by Gury et al. (2004) or by Perea Vélez et al., 2007, or by means of the technique known as "genome shuffling" (Patnaik et al., 2002 and Wang et al., 2007).

A subject of the present invention is also cell fractions which can be obtained from the *Lactobacillus rhamnosus* strain as defined above, preferably the strain CNCM I-4719. They are in particular DNA preparations or bacterial wall preparations obtained from cultures of said strain. They may also be culture supernatants or fractions of these supernatants. By way of example, cell-free supernatant (CFS) of the strain CNCM I-4719 can be obtained using the method for obtaining a CFS from another *Lactobacillus rhamnosus* strain.

A subject of the present invention is also a method for obtaining a cell fraction, comprising the steps of:

a) culturing a *L. bulgaricus* strain as defined above, preferably the strain CNCM I-4719, and b) obtaining and/or recovering the cell fraction from the culture in step a).

In compositions of the invention, said strain can be used in the form of whole bacteria which may be living or dead. Alternatively, said strain can be used in the form of a bacterial lysate or in the form of bacterial fractions; the bacterial fractions suitable for this use can be chosen, for example, by testing their properties on mercury removal from an aqueous environment. Preferably the bacterial cells are present as living, viable cells.

Food—Grade Bacteria for Removing Toxic Compounds

In one embodiment, the present invention relates to food-grade bacterial or extracts thereof, including probiotics, capable of removing or sequestering toxic compounds from an environment to which the food-grade bacteria is exposed to, or from a substance. Substances may include edible compositions, such as vegetable-based foods or animal-based foods, and may also include drinkable solutions, including water, milk, syrups, extracts and other beverages. Substances may also include raw agricultural products used to produce foods and drinkable solutions. As such, the present invention relates also to methods of using the food-grade bacteria of the present invention to prevent the uptake of toxic compounds by a subject, or in methods to filter toxic compounds out of substances prior to exposing a subject to said substances.

The food grade bacteria may be any type of bacteria that may be capable of removing toxic compounds from foods or solutions that may be consumed by a subject, or from ingredients used in the manufacture of said foods or solutions. Table 1 includes food-grade bacteria that may be used with the present invention. In a preferred aspect, the food-grade bacteria may be aerobically, microaerophilically or anaerobically grown and may be selected from the group consisting of the food-grade bacteria of Table 1. Administration of the food-grade bacteria, or extract thereof, to a subject may be accomplished by any method likely to introduce the organisms into the gastro-intestinal tract of the subject. The bacteria can be mixed with a carrier and applied to liquid or solid feed or to drinking water. The carrier material should be non-toxic to the subject. When dealing with live food-grade bacteria, the carrier material should also be non-toxic to the food-grade bacteria. When dealing with live food-grade bacteria the carrier, preferably, may include an ingredient that promotes viability of the bacteria during storage. The food-grade bacteria may also be formulated as an inoculant paste to be directly injected into a subject's mouth. The formulation may include added ingredients to improve palatability, improve shelf-life, impart nutritional benefits, and the like. If a reproducible and measured dose is desired, the food-grade bacteria can be administered by a cannula or syringe. The amount of food-grade bacteria to be administered is governed by factors affecting efficacy. When administered in feed or drinking water the dosage can be spread over a period of days or even weeks. The cumulative effect of lower doses administered over several days may be greater than a single larger dose thereof. One or more strains of food-grade bacteria may be administered together. A combination of strains may be advantageous because individual subjects may differ as to the strain which is most persistent in a given individual.

The present invention is also directed to extracts or fragments of food-grade bacterial that may be capable of removing or sequestering toxic compounds from a substance or sample. As shown herein, the inventors found that dead food-grade bacteria may be used to sequester mercury from a sample. As such the present invention is directed to food-grade bacteria fragments capable of binding toxic compounds found in a substance of interest.

Applications

Food-grade bacteria of the present invention may be administered as a preventive measure, to prevent a subject not presently carrying a toxic compound, from acquiring the toxic compound by exposure to consumables or environments where the toxic compounds are present.

Treatment of a subject carrying the toxic compounds may be accomplished to reduce or eliminate the amount of the toxic compound carried by the subject, by administering the food-grade bacteria, or extracts thereof, to the subject carrying the toxic compound.

The methods for administering food-grade bacteria are essentially the same, whether for prevention or treatment. By routinely administering an effective dose to a subject, the risk of contamination by the undesired toxin may be substantially reduced or eliminated by a combination of prevention and treatment.

In one embodiment, food-grade bacteria of the present invention may be used in methods to filter toxic compounds out of a substance. The method, in one embodiment, may comprise contacting the substance with the food-grade bacteria for a sufficient amount of time, and removing the food-grade bacteria and the toxin from the sample.

To accomplish this filtration of toxic compounds from a substance, the food-grade bacteria, extracts or fragments of said food-grade bacteria capable of binding to the toxic compounds, may be attached to a filter, or to a solid support, such as an affinity column, and the substance may then be run through the filter or affinity column.

Food-grade bacteria may also be used, according to another embodiment of the present invention, to feed aquatic animals such as fish and shrimp. In one embodiment, food-grade bacteria of the present invention may be added to tanks and ponds containing the aquatic animal. Preferably the food-grade bacteria used for aquatic animals, may be a bacteria that occurs naturally in fresh and sea water environments.

Preparation and Administration

Although this invention is not intended to be limited to any particular mode of application, oral administration of the compositions are preferred. One food-grade bacterium may be administered alone or in conjunction with a second, different food grade bacterium. Any number of different food-grade bacteria may be used in conjunction. By "in conjunction with" is meant together, substantially simultaneously or sequentially. The compositions may be administered in the form of tablet, pill or capsule, for example. One preferred form of application involves the preparation of a freeze-dried capsule comprising the composition of the present invention. Another preferred form of application involves the preparation of a lyophilized capsule of the present invention. Still another preferred form of application involves the preparation of a heat dried capsule of the present invention.

By "amount effective" as used herein is meant an amount of food-grade bacterium or bacteria, e.g., $Lactobacillus$, high enough to significantly positively modify the condition to be treated but low enough to avoid serious side effects (at a reasonable benefit/risk ratio), within the scope of sound medical judgment. An effective amount of $Lactobacillus$ will vary with the particular goal to be achieved, the age and physical condition of the subject being treated, the duration of treatment, the nature of concurrent therapy and the specific $Lactobacillus$ employed. The effective amount of $Lactobacillus$ will thus be the minimum amount which will provide the desired detoxification.

A decided practical advantage is that the food-grade bacteria, e.g. $Lactobacillus$, may be administered in a convenient manner such as by the oral, intravenous (where non-viable), or suppository (vaginal or rectal) routes. Depending on the route of administration, the active ingredients which comprise food-grade bacteria may be required to be coated in a material to protect said organisms from the action of enzymes, acids and other natural conditions which may inactivate said organisms. In order to administer food-grade bacteria by other than parenteral administration, they should be coated by, or administered with, a material to prevent inactivation. For example, food-grade bacteria may be co-administered with enzyme inhibitors or in liposomes. Enzyme inhibitors include pancreatic trypsin inhibitor, diisopropylfluorophosphate (DFP) and trasylol. Liposomes include water-in-oil-in-water P40 emulsions as well as conventional and specifically designed liposomes which transport $lactobacilli$ or their by-products to an internal target of a host subject.

The food-grade organisms may also be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage. The carrier can be a solvent or dispersion medium containing, for example, water, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the food-grade bacteria in the required amount in the appropriate solvent with various of the other ingredients enumerated above, as required, followed by filtered sterilization. Generally, dispersions are prepared by incorporating the various sterilized food-grade bacteria into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from previously sterile-filtered solution thereof. Additional preferred methods of preparation include but are not limited to lyophilization and heat-drying.

When the food-grade bacteria are suitably protected as described above, the active compound may be orally administered, for example, with an inert diluent or with an assimilable edible carrier, or it may be enclosed in hard or soft shell gelatin capsule, or it may be compressed into tablets designed to pass through the stomach (i.e., enteric coated), or it may be incorporated directly with the food of the diet. For oral therapeutic administration, the food-grade bacteria may be incorporated with excipients and used in the form of ingestible tablets, buccal tablets, troches, capsules, elixirs, suspensions, syrups, wafers, and the like.

The tablets, troches, pills, capsules, and the like, as described above, may also contain the following: a binder such as gum tragacanth, acacia, corn starch or gelatin; excipients such as dicalcium phosphate: a disintegrating agent such as corn starch, potato starch, alginic acid, and the like: a lubricant such as magnesium stearate: and a sweetening agent such as sucrose, lactose or saccharin may be added or a flavoring agent such as peppermint, oil or wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules or $lactobacilli$ in suspension may be coated with shellac, sugar or both.

A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the food-grade organism may be incorporated into sustained-release preparations and formulations.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of the food-grade bacteria calculated to produce the desired preventive or therapeutic effect in association with the required pharmaceutical carrier. The specification for the novel dosage unit forms of the invention may be dictated by and may be directly depending on (a) the unique characteristics of the food-grade bacteria and the particular preventive, detoxification or therapeutic effect to be achieved, and (b) the limitations inherent in the art of compounding such food-grade bacteria for the establishment and maintenance of a healthy flora in the intestinal tract.

The food-grade organism is compounded for convenient and effective administration in effective amounts with a suitable pharmaceutically or food acceptable carrier in dosage unit form as hereinbefore disclosed. A unit dosage form can, for example, contain the principal active compound in an amount approximating $10^9$ viable or non-viable, e.g., lactobacilli, per ml. In the case of compositions containing supplementary ingredients such as prebiotics, the dosages are determined by reference to the usual dose and manner of administration of the said ingredients.

The pharmaceutically acceptable carrier may be in the form of milk or portions thereof including yogurt. Skim milk, skim milk powder, non-milk or non-lactose containing products may also be employed. The skim milk powder is conventionally suspended in phosphate buffered saline (PBS), autoclaved or filtered to eradicate proteinaceous and living contaminants, then freeze dried heat dried, vacuum dried, or lyophilized.

Some other examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; calcium carbonate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; cranberry. extracts and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tabletting agents, stabilizers, anti-oxidants and preservatives, can also be present.

Accordingly, the subject may be orally administered a therapeutically effective amount of at least one food-grade bacteria and a pharmaceutically acceptable carrier in accordance with the present invention.

TABLE 1

Comparative *Lactobacillus rhamnosus* strains

| Strain code 1 | Strain code 2 |
|---|---|
| HN001 | |
| R37 | DN 116-0060 |
| R38 | DN 116-0063 |
| R22 | DN 116-0009 |
| R17 | DN 116-0136 |
| R29 | DN 116-0064 |
| R3 | DN 116-0061 |
| R10 | DN 116-0032 |
| R11 | DN 116-0141 |

The above disclosure generally describes the present invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Example 1

Demonstration of Removal of Inorganic Mercury from an Aqueous Environment

A 1% inoculum of a 24 hour culture of *Lactobacillus rhamnosus* DN116-060 was added to de Man Rogosa Sharpe (MRS) broth containing $HgCl_2$ and incubated for 24 hours at 37° C. Following incubation, cells were removed by centrifugation at 5,000 g. The total mercury concentration in the supernatant was analyzed via cold vapor atomic absorption spectroscopy (CVAAS). As illustrated in FIG. 1, the lactobacilli removed 94.4% of a 1 part per million (ppm) mercury inoculum (FIG. 1A) and 85% of a 15 part per billion (ppb) inoculum (FIG. 1B). Both removals were deemed significant ($p<0.05$) by an unpaired T-test.

Example 2

Demonstration of Removal of Organic Mercury Form an Aqueous Environment

A 1% inoculum of a 24 hour culture of *L. rhamnosus* DN116-060 was added to de Man Rogosa Sharpe (MRS) broth containing MeHgCl2 and incubated for 24 hours at 37° C. Following incubation, cells were removed by centrifugation at 5,000 g. The total mercury concentration in the supernatant was analyzed via cold vapor atomic absorption spectroscopy (CVAAS).

Figure 2:
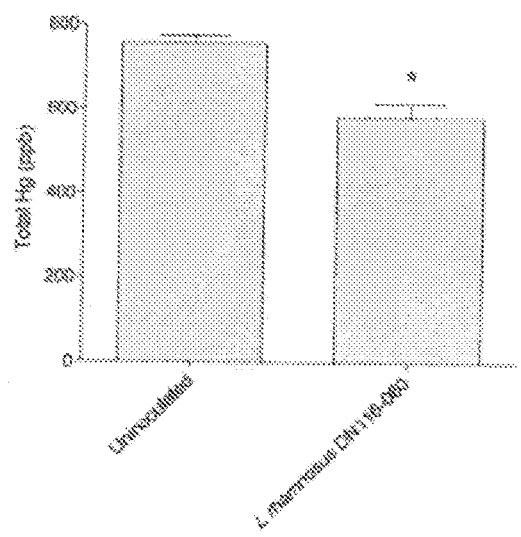
FIG. 2 is a graph illustrating the ability of a food grade bacterium of the present invention to remove organic mercury from a solution (error bars±SEM; * signifies significant (p<0.05) difference by an unpaired T-test).

FIG. 2 shows the ability of a food grade bacterium to remove $MeHg^{2+}$ from solution at a starting inoculum of 1 ppm MeHgCl2. (Error bars±SEM). As illustrated in FIG. 2, the lactobacilli removed 23.2% of a 1 ppm mercury inoculum ($p<0.05$ by an unpaired t-test).

Example 3

Inorganic Mercury Removal by Live and Dead *Lactobacillus rhamnosus* DN116-060

The assay was carried out as previously described in Example 1 at a concentration of 500 ppb $HgCl_2$. Viable cells of *Lactobacillus rhamnosus* DN116-010 were compared to cells that were killed by heating at 80° C. for 10 minutes at an inoculum equivalent to the final cell density of viable cells.

Figure 3:
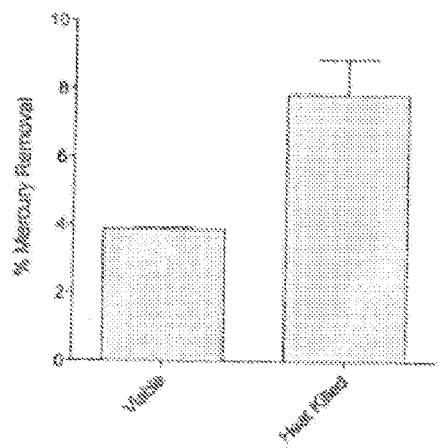
FIG. 3 is a graph illustrating the ability of live and dead food grade bacterium of the present invention to remove inorganic mercury from a solution (error bars±SEM; * signifies significant (p<0.05) difference by an unpaired T-test).

FIG. 3 illustrates the ability of live and dead *Lactobacillus rhamnosus* DN116-060 to remove $Hg^{2+}$ from solution at a starting inoculum of 500 ppb $HgCl_2$. As shown in FIG. 3, viable cells were capable of removing significantly more mercury than heat killed cells ($p<0.05$ by unpaired t-test) suggesting that there is a passive sequestering of mercury as well as potential metabolic detoxification.

Example 4

Variability of Mercury Resistance within Food Grade *Lactobacillus rhamnosus* Bacteria Assay was carried out as previously described in Example 1 across a spectrum of $HgCl_2$ concentrations. Growth was measured after 24 hours at 37° C. by the optical density of cultures at a wavelength of 600 nm. A spectrum of resistances to mercury were observed in both species demonstrating that resistance to mercury is a variable trait among food grade bacteria.

Figure 4:
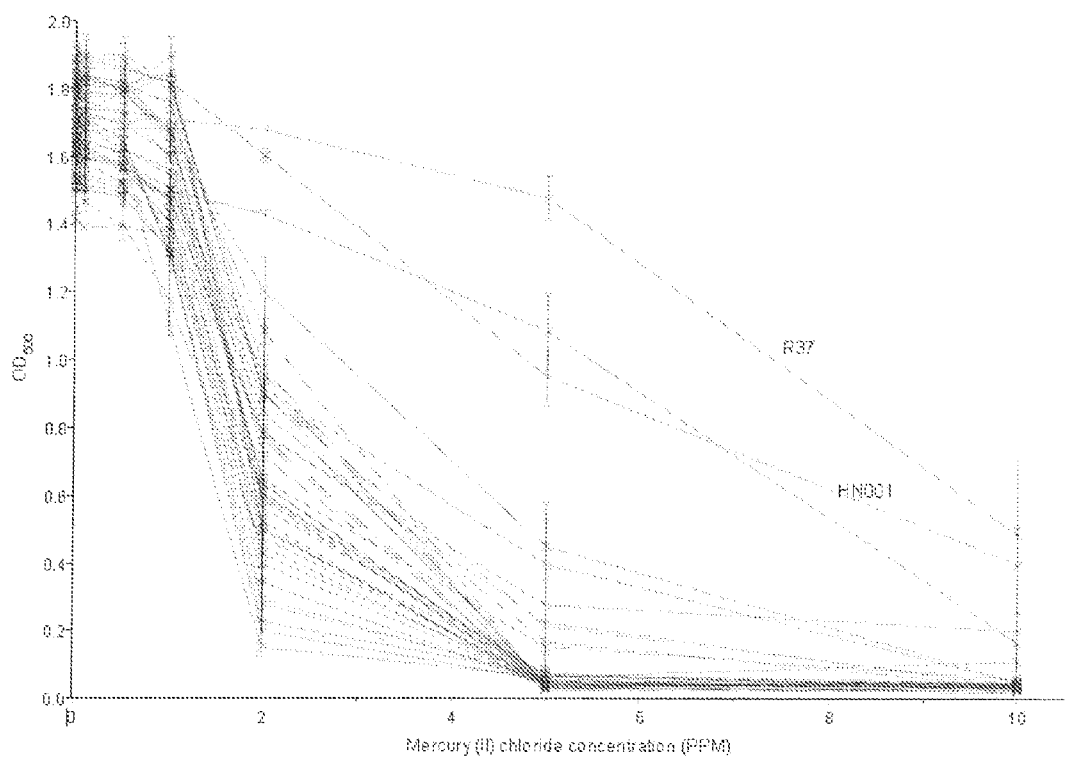
FIG. 4 is a graph illustrating variability of mercury resistance within a group of food grade bacteria of the genus *Lactobacillus rhamnosus* in a gradient of $Hg^{2+}$.

FIG. 4 illustrates the growth of 40 different strains of *Lactobacillus rhamnosus*, including the comparative strains of Table 1, in a gradient of $Hg^{2+}$ measured by OD600 after 24 hours incubation at 37° C. Each set of connected points represents one strain. Resistance is a strain variable trait resulting in a spectrum of resistance profiles in both species. FIG. 4 illustrates that *Lactobacillus Rhamnosus* strain DN 116-060, also referred to as "R37" has a much higher resistance as compared to the rest of the strains, including strain HN001.

The invention claimed is:

1. A method for providing a genetically modified strain of *Lactobacillus rhamnosus*, comprising:
   providing the *Lactobacillus rhamnosus* strain DN 116-0060 (deposited with the Collection Nationale de Cultures de Microorganisms (CNCM) under number I-4719); and
   genetically modifying the *Lactobacillus rhamnosus* strain DN 116-0060 by at least one of mutagenesis and genetic transformation to thereby provide the genetically modified strain of *Lactobacillus rhamnosus*.

2. A method for obtaining a cell fraction lysate comprising:
   a) providing the *Lactobacillus rhamnosus* strain DN 116-0060 (deposited with the Collection Nationale de Cultures de Microorganisms (CNCM) under number I-4719),
   b) genetically modifying the *Lactobacillus rhamnosus* strain DN 116-0060 by at least one of mutagenesis and genetic transformation to thereby provide a genetically modified strain of *Lactobacillus rhamnosus*, and
   c) recovering the cell lysate from the culture; wherein the cell lysate is capable of removing mercury from an aqueous environment.

3. A cell lysate obtained by the method of claim 2.

4. A composition comprising the cell lysate according to claim 3.

5. The composition according to claim 4, further comprising a carrier.

6. The composition according to claim 5, wherein the carrier is a milk-based product.

7. A composition for administration to a subject, comprising:
   *Lactobacillus rhamnosus* strain DN 116-0060 (deposited with the Collection Nationale de Cultures de Microorganisms (CNCM) under number I-4719) or a cell lysate thereof; and
   an effective amount of a protective agent that protects the *Lactobacillus rhamnosus* strain DN 116-0060, or cell lysate thereof, in the composition from inactivation during administration to a subject.

8. The composition according to claim 7, wherein the composition is formulated for oral administration and the protective agent is an enzyme inhibitor.

9. The composition according to claim 8, wherein the enzyme inhibitor is selected from pancreatic trypsin inhibitor, diisopropylfluorophosphate (DFP), and trasylol.

10. The composition according to claim 8, wherein the composition is formulated for oral administration and the protective agent is a liposome.

11. The composition according to claim 10, wherein the liposome is a water-in-oil-in-water P40 emulsion.

12. The composition according to claim 7, wherein the cell lysate is obtained by a method comprising:
   culturing *Lactobacillus rhamnosus* strain DN 116-0060; and
   recovering the cell lysate from the culture.

13. The composition according to claim 7, further comprising a carrier.

14. The composition according to claim 13, wherein the carrier is a milk-based product.

15. A composition comprising:
   yogurt; and
   *Lactobacillus rhamnosus* strain DN 116-0060 (deposited with the Collection Nationale de Cultures de Microorganisms (CNCM) under number I-4719) or a cell lysate thereof;
   wherein the *Lactobacillus rhamnosus* strain DN 116-0060 or cell lysate thereof is dispersed throughout the yogurt.

* * * * *